Oct. 29, 1968 MASAMI UTSUMI Plant Pat. 2,842
RED POINSETTIA PLANT
Filed March 9, 1967
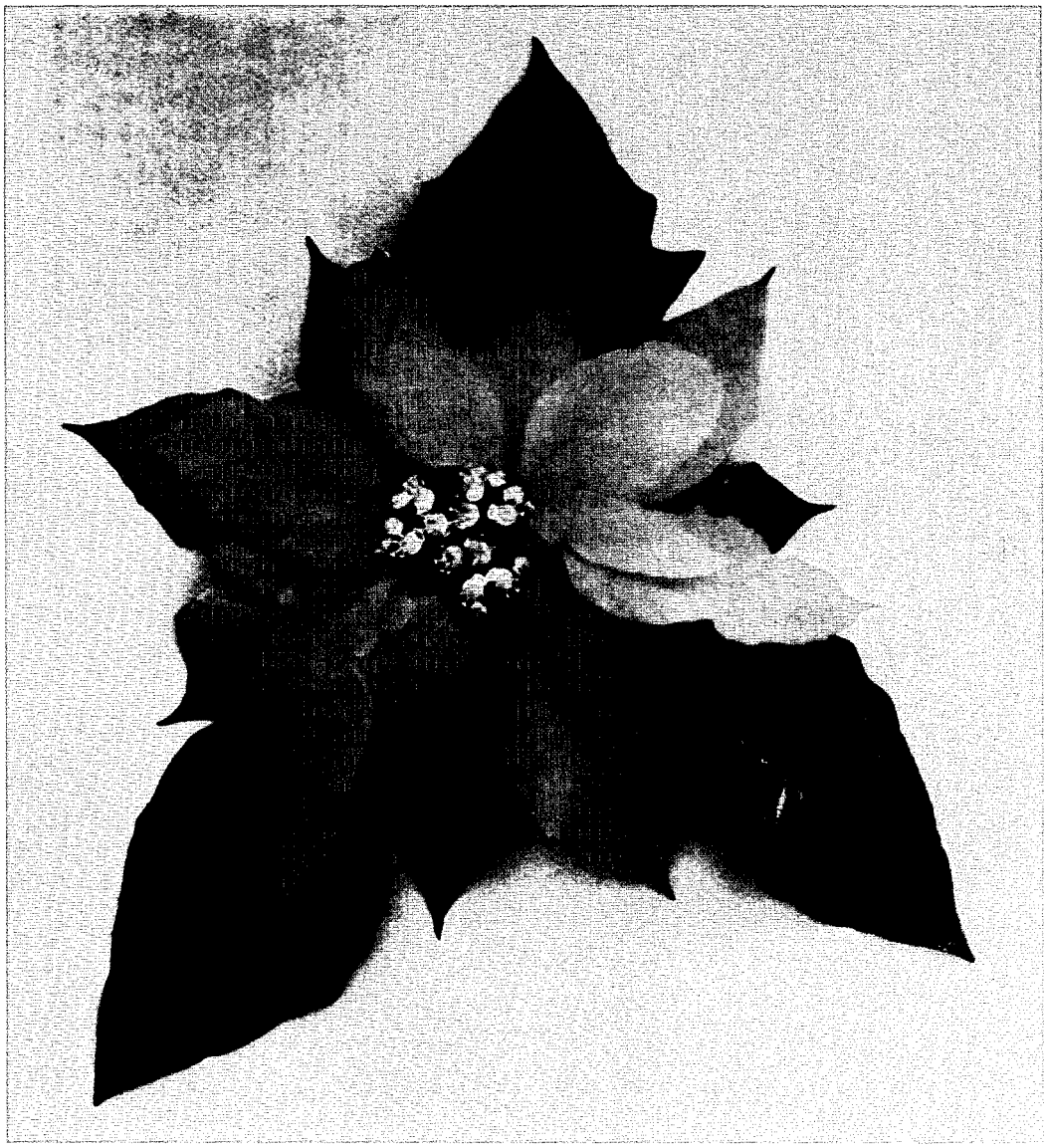
INVENTOR
MASAMI UTSUMI
BY Rummler & Snow
Attys -

United States Patent Office

Plant Pat. 2,842
Patented Oct. 29, 1968

2,842

RED POINSETTIA PLANT

Masami Utsumi, 3701 Prescott Ave., Lincoln, Nebr. 68506

Filed Mar. 9, 1967, Ser. No. 622,003
1 Claim. (Cl. Plt.—86)

ABSTRACT OF THE DISCLOSURE

This invention concerns a new and distinct variety of poinsettia plant, characterized by the extraordinary deep red color of its bracts, which persist for up to two and one-half months under normal indoor conditions, by its sturdy, green, closely-spaced leaves which persist from the base of the plant upward, thereby avoiding bare stem bases for the showy bracts, and by the close-to-stem grouping of its bracts to provide a relatively large, substantially solid display of color at the end of each stalk.

*Background of the invention*

This new variety of poinsettia plant originated as a seedling of the variety Ecke White (unpatented) as the seed parent and an unnamed red seedling, of unknown parentage, as the pollen parent, and was developed by me in the course of a ten-year breeding program carried on by me at Lincoln, Nebr., with the object of producing a more sturdy and long-lasting red poinsettia plant of average 15-inch height, having a more abundant production of leaves and bracts, a more compact grouping of the bracts on short petioles so as to present a more attractive display of color at the end of each main stem, and to produce a red poinsettia plant that will be more tolerable to adverse temperature conditions in stores and homes where the plants are displayed.

This new variety has been asexually reproduced by me in my greenhouses at Lincoln, Nebr., and successive generations produced asexually by means of cuttings have demonstrated that the novel and advantageous characteristics of the new variety hold true from generation to generation.

*Description of the drawing*

My new variety of poinsettia plant is illustrated in the accompanying full color drawing which shows a typical display of the inflorescence and the leaves as they appear at the top of each main stem.

*Description of the new plant variety*

The following is a detailed description of my new variety of poinsettia with color designation according to the Horticultural Color Chart of the British Color Council.

Origin: Seedling.
Parentage:
*Seed parent.*—Ecke White (unpatented).
*Pollen parent.*—An unnamed red seedling (unpatented) of unknown parentage.
Classification:
*Botanic.*—*Euphorbia pulcherrima.*
*Commercial.*—Poinsettia.
Form: Shrub.
Growth: Upright, rapid and vigorous.
Height: 12 to 18 inches, averaging 15 inches.
Strength: Very strong and sturdy.
Branching: None, unless decapitated.
Foliage:
*Leaves.*—Abundant, 10 to 14 per stalk. Size—9 to 10 cm. wide x 13 to 16 cm. long. Shape—ovate and elliptic, with entire margin. Texture—smooth. Color: upper side—Cypress Green 245; under side—nearly Moss Green 83. Petioles—length 5 to 6 cm. Ribs and veins—pinnate and prominent.

*Bracts.*—Number—averages 20 per stalk. Size—3 x 5.5 cm. to 8 x 15 cm. Shape—generally elliptic, acuminate tip, entire margin. Arrangement—generally overlapping, 8 to 10 inch diameter of spread. Petioles—short, 1 to 1.5 cm., red in color. Color—most nearly Currant Red 23. Appearance—velvety.
*Lasting quality.*—Bracts and flowers persist for two to two and one-half months on the plant. One week as a cut flower.
*Disease resistance.*—Resistant to root rot, leaf spot, and bacterial canker, as tested and observed at Lincoln, Nebr., under conditions where such diseases were present in other plants.
Blooms: Sparsely once each year in late fall. The cymose flowers have single, terminal anthers 0.3 mm. long and red colored filaments 5.0 mm. long. Each flower has one pistil 5.0 mm. long and the stigmas are raspberry red 316 in color. The pollen is yellow and the ovaries are three-parted with a central placenta.

In general, the bract and foliage retention of my new variety of poinsettia plant is like that of Mikkelpink (P.P. 2,501) and extensive propagation of the new variety shows the bract retention to be as long lasting as Ecke White (unpatented). Also, the foliage persists from the base of the stem to the bract in a manner similar to Paul Mikkelsen (P.P. 2,328) thereby avoiding bare stem conditions as the plant ages. The bract formation is larger, however, as in the case of Indianapolis Red (P.P. 1,068) and the bracts form in the same position and manner as Barbara Ecke Supreme (P.P. 1,055).

The color of the bract of my new variety is different from any other poinsettia in that it is of a deeper red with a plush-like appearance, and the over-all display of the inflorescence of the new variety, with its wide spread of solid deep red against the dark green of the closely spaced leaves, provides a more beautiful and attractive appearance than most other varieties of red poinsettia.

The bracts and foliage of the new variety tolerate adverse retail store and consumer house temperature changes and the long bract and foliage retention characteristics allow a longer selling program for green houses and retail stores, thus making the new variety of poinsettia commercially attractive and advantageous.

For the grower, the new variety has the advantageous faculty of branching easily, when decapitated, for an abundant production of cuttings from a single stalk. The cuttings form an opulent root structure within ten to fourteen days in the manner of Ecke Pink (unpatented). Also, an advantage of panning the new variety is that it does not require a growth retardant to obtain an average height of about fifteen inches under normal glass-house production conditions.

I claim:

1. A new and distinct variety of poinsettia plant substantially as herein shown and described, distinguished by the deep velvety red color of its numerous and closely spaced bracts which grow on unusually short petioles to produce a wide, substantially solid color display, by the persistence of its foliage and bracts to retention on the talk for long periods and under the adverse conditions of normal store and home temperature changes, by the abundance of its leaves which persist from base to bract, and by its rapid and vigorous upright growth to an average mature height of about fifteen inches.

No references cited.

ROBERT E. BAGWILL, *Primary Examiner.*